(12) United States Patent
Diekmann

(10) Patent No.: US 11,209,385 B2
(45) Date of Patent: *Dec. 28, 2021

(54) METHOD FOR TESTING A GAS SENSOR AND GAS-MEASURING DEVICE WITH A TESTING DEVICE FOR TESTING A GAS SENSOR

(71) Applicant: Dräger Safety AG & Co. KGaA, Lübeck (DE)

(72) Inventor: Wilfried Diekmann, Utecht (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 451 days.

This patent is subject to a terminal disclaimer.

(21) Appl. No.: 15/460,748

(22) Filed: Mar. 16, 2017

(65) Prior Publication Data

US 2017/0269026 A1    Sep. 21, 2017

(30) Foreign Application Priority Data

Mar. 18, 2016  (DE) ................ 10 2016 003 284.7

(51) Int. Cl.
*G01N 27/416* (2006.01)
*G01N 27/414* (2006.01)
*G01N 33/00* (2006.01)

(52) U.S. Cl.
CPC ..... *G01N 27/4163* (2013.01); *G01N 27/4141* (2013.01); *G01N 33/007* (2013.01); *G01N 2033/0072* (2013.01)

(58) Field of Classification Search
CPC ........ G01N 27/406–41; G01N 33/0004–0075; G01N 27/4163; G01N 27/4141; G01N 33/007; G01N 2033/0072
See application file for complete search history.

(56) References Cited

U.S. PATENT DOCUMENTS

| 4,151,739 | A | * | 5/1979 | Breuer ............... G01N 33/0006 73/1.06 |
| 4,267,030 | A | | 5/1981 | Breuer et al. |
| 4,338,281 | A | | 7/1982 | Treitinger et al. |
| 4,854,155 | A | | 8/1989 | Poli |
| 5,565,075 | A | | 10/1996 | Davis et al. |

(Continued)

FOREIGN PATENT DOCUMENTS

| CH | 624 488 A5 | 7/1981 |
| CN | 102087242 A | 6/2011 |

(Continued)

OTHER PUBLICATIONS

Pleisch et al. (EP 1281957 A1, Machine Translation) (Year: 2001).*

*Primary Examiner* — Joshua L Allen
(74) *Attorney, Agent, or Firm* — McGlew and Tuttle, P.C.

(57) ABSTRACT

A method for testing a gas sensor and a gas-measuring device with a testing device for testing the gas sensor provides an improved analysis and evaluation of states of gas sensors. Due to a testing of a gas admission element, by monitoring measuring signals (35, (38) in a time course (400) in conjunction with dispensing (91, 91', 91") a quantity of test substance, it is made possible to check whether a gas supply to the gas sensor is possible (to check if the gas diffusion path is open) and given.

20 Claims, 5 Drawing Sheets

(56) References Cited

U.S. PATENT DOCUMENTS

| | | | | |
|---|---|---|---|---|
| 6,182,497 | B1* | 2/2001 | Krajci | G01N 33/0075 340/605 |
| 7,406,854 | B2* | 8/2008 | Lange | G01N 21/09 73/1.06 |
| 7,645,367 | B2* | 1/2010 | Tschuncky | G01N 33/0006 204/401 |
| 10,132,786 | B2* | 11/2018 | Diekmann | G01N 33/0011 |
| 2004/0007667 | A1* | 1/2004 | Diekmann | G01N 21/3504 250/343 |
| 2005/0247878 | A1* | 11/2005 | Baschant | G01N 21/3504 250/343 |
| 2005/0262924 | A1* | 12/2005 | Wood | G01N 33/0006 73/31.05 |
| 2006/0266096 | A1* | 11/2006 | Eickhoff | G01N 33/0006 73/1.06 |
| 2006/0283707 | A1* | 12/2006 | Kuhn | G01N 33/0006 204/424 |
| 2008/0078671 | A1* | 4/2008 | Caro | C25B 3/04 204/230.2 |
| 2011/0108418 | A1* | 5/2011 | Nauber | G01N 33/007 204/409 |
| 2013/0074575 | A1* | 3/2013 | Duric | G01N 33/0006 73/1.03 |
| 2013/0192332 | A1 | 8/2013 | Scheffler et al. | |
| 2013/0265579 | A1* | 10/2013 | Beckmann | G01N 21/17 356/437 |
| 2014/0290328 | A1* | 10/2014 | Wang | G01N 33/007 73/1.06 |
| 2014/0331737 | A1* | 11/2014 | Kaneblei | G01N 33/0006 73/1.06 |
| 2017/0016866 | A1* | 1/2017 | Chey | C23C 14/34 |

FOREIGN PATENT DOCUMENTS

| | | | | |
|---|---|---|---|---|
| CN | 102798698 A | 11/2012 | | |
| CN | 103399123 A | 11/2013 | | |
| CN | 104807968 A | 7/2015 | | |
| DE | 10 2006 045055 B3 | 2/2008 | | |
| DE | 20 2006 020 536 U1 | 11/2008 | | |
| DE | 10 2009 052 957 A1 | 6/2011 | | |
| EP | 0744620 A1 * | 11/1996 | | G01N 27/404 |
| EP | 1 281 957 A1 | 2/2003 | | |
| EP | 1281957 A1 * | 2/2003 | | G01N 33/007 |
| EP | 2 639 583 A1 | 9/2013 | | |
| EP | 2 887 062 A2 | 6/2015 | | |
| GB | 2254696 A * | 10/1992 | | G01N 27/404 |
| GB | 2 356 708 A | 5/2001 | | |
| WO | 99/17110 A1 | 4/1999 | | |
| WO | WO-9917110 A1 * | 4/1999 | | G01N 33/0006 |
| WO | 02/091326 A1 | 11/2002 | | |

* cited by examiner

METHOD FOR TESTING A GAS SENSOR AND GAS-MEASURING DEVICE WITH A TESTING DEVICE FOR TESTING A GAS SENSOR

CROSS REFERENCE TO RELATED APPLICATIONS

This application claims the benefit of priority under 35 U.S.C. § 119 of German Application 10 2016 003 284.7, filed Mar. 18, 2016, the entire contents of which are incorporated herein by reference.

FIELD OF THE INVENTION

The present invention pertains to a method for testing a gas sensor as well as to a testing device for testing the gas sensor of a gas-measuring device.

BACKGROUND OF THE INVENTION

Gas-measuring devices are used for industrial gas measurement and protect persons who are located in industrial areas or in buildings in which gases that are hazardous for health, be they process gases or waste gases, may be present, from risk to health and life.

Industrial gases are monitored by gas-measuring devices in industrial environments, for example, in the chemical or petrochemical industry, to determine whether these gases are associated with hazards based on explosive or toxic properties. Gas-measuring apparatus or gas-measuring devices used stationarily are used in many cases. Infrared-optical measuring sensors, electrochemical sensors, catalytic sensors or semiconductor gas sensors are usually used as sensors in such gas-measuring devices.

It is important for the reliability of the gas-measuring devices as well as of the alarms and warnings generated thereby, that the gas-measuring devices be fully able to function during the operation and that malfunctions be reliably detected.

A thin-layer semiconductor gas sensor is described in U.S. Pat. No. 4,338,281A. The thin-layer semiconductor gas sensor has an integrated heating element. It is a metal oxide semiconductor, in which the electrical resistance of the metal oxide semiconductor layer has a value that is dependent as a function of the concentration of the gas to be detected. This change in resistance can be measured as an indicator of the presence of the gas to be detected by a suitable electronic analyzing unit associated with the thin-layer semiconductor sensor.

A catalytically operating detector circuit for combustible gases is described in U.S. Pat. No. 4,854,155 A. The detectors for the combustible gases are configured as sensor resistor elements with a catalytic coating. Detectors for combustible gases are used to detect the presence of combustible gases that may occur, for example, in mines or industrial plants.

U.S. Pat. No. 5,565,075 A describes an electrochemical gas sensor for detecting nitrogen monoxide. In a housing filled with an electrolyte, the sensor has a working electrode, a reference electrode and a counterelectrode.

Such an electrochemical gas sensor can preferably be used for medical applications, because it has a low cross sensitivity to other gases usually used in this environment.

U.S. 2005/0247878 A1 describes an infrared gas sensor. Two infrared radiation detectors arranged next to each other are arranged in a housing on one side of the housing, while a radiation source, which emits infrared radiation, is arranged on the other side. Gas to be analyzed is introduced into the beam path from a measuring environment.

The measurement effect is based on the fact that the light emitted by the radiation source is attenuated as a function of the gas species in the beam path. One of the two detectors is operated as a reference detector, while the other detector is operated as a measuring detector. The concentration of the gas introduced into the beam path is determined from the ratio of the signals of the measuring detector and of the reference detector.

In many application situations, such gas sensors are combined or developed into stationary gas-measuring devices. Stationary gas-measuring devices are often and usually distributed in industrial plants as a plurality of sensor units for gas measurement over a plurality of rooms or larger areas.

U.S. Pat. No. 6,182,497 B1 describes a gas-measuring system, which is configured to connect a plurality of sensors to a central analysis unit. The sensors may be connected, for example, via a universal, serial bus.

A gas sensor with an adapter is known from U.S. Pat. No. 7,406,854 B2. The adapter is configured for connecting a flexible tube. It is possible via this flexible tube to deliver gases from a remotely located measuring site or a measured gas or a calibrating gas to the gas sensor for testing the ability of the gas sensor to function. Measured gas or calibrating gas may be delivered, for example, by means of a feed pump.

WO 1999/17110 A1 as well as U.S. Pat. No. 7,645,367 B2 disclose gas-measuring systems comprising a gas sensor and a gas generator. Such combinations of gas generators and gas sensors make it possible to test the measuring properties of the gas sensors, especially to determine whether the gas sensor responds sensitively to the admission of a predefined measured gas concentration.

A device for testing a gas sensor is known, for example, from DE 20 2006 020 536 U1. A gas generator, which is suitable for generating ethane, is described there. The gas generator is intended for testing the gas sensor and is configured to dispense a certain quantity of a test gas to/into the gas sensor, and a resulting change or reaction of the output signal of the gas sensor represents an indication of the ability of the gas sensor to function.

The U.S. Occupational Safety Administration (OSHA) has recommendations for function tests with so-called "bump tests," in which a regular testing of gas sensors is to be performed by means of suitable adapters and a suitable test gas.

U.S. Pat. No. 7,406,854 B2 describes an adapter for testing or calibrating an electrochemical gas sensor. The adapter can preferably be placed on the gas sensor with a Velcro fastener and can be removed from same after completion of the testing or calibration.

There is a need for a regular testing of the ability of the gas sensors to function especially for already existing plants or installations of gas-measuring systems. In particular, there is a need for the testing of the gas sensors to be able to be performed without removal or disassembly of the gas sensors being necessary at the given measuring site in the plant. The testing of gas sensors in already existing gas-measuring systems shall be made possible without complicated manual operations performed by maintenance workers being necessary, for example, in case of the use of the adapter according to U.S. Pat. No. 7,406,854 B2, because it would otherwise be necessary for the maintenance workers in a larger industrial plant to mount the adapter for the subsequent testing of the sensors and then to remove the adapter manually when the gas sensor is put into operation. Furthermore, there is need for determining that gas sensors that deliver a gas concentration measured value as an output signal, from which the absence of harmful gases, i.e., a trouble-free situation, can be inferred, are indeed in an effective gas exchange with the measuring environment at the measuring site with the sensor-active elements. Consequently, there is a need for avoiding misinterpretations, especially of constant, noncritical gas concentration measured values or other constant output signals of the gas sensor.

SUMMARY OF THE INVENTION

With the knowledge of the above-mentioned state of the art, an object of the present invention is to provide a method for testing a gas sensor, which makes it possible to determine whether an unhindered supply of gas from a measuring environment to the gas sensor is possible.

Another object of the present invention is to provide a testing device, which makes it possible to carry out the method for testing a gas sensor.

Features and details that are described in connection with the method according to the present invention for testing the gas sensor also apply, of course, in connection with and in respect to the gas-measuring device suitable for carrying out the method and vice versa, so that reference is and can always mutually be made to the individual aspects of the present invention with respect to the disclosure.

The present invention is based on a test gas dispensing unit, which is arranged at a gas sensor in a gas-measuring arrangement or in a gas-measuring device, which is operated to monitor or check whether an unhindered supply of gas into the gas sensor through at least one gas admission element present in a gas-measuring arrangement or gas-measuring device is given and thus to check whether the gas sensor is ready to operate.

Some of the terms used in connection with this patent application will be explained in more detail at the beginning.

An output signal or a measured signal, as well as a sensor signal is defined in the sense of the present invention as a signal which is provided by the gas sensor and which represents a gas concentration measured value. The output signal or the measured signal may be provided here by the gas sensor as a voltage signal, e.g., in a voltage range of 0 V to 10 V; a current signal, e.g., as a so-called 4-mA . . . 20-mA output signal; as digital data words by means of data lines and/or different interfaces and protocols, such as RS232, RS485, NMEA183, USB, CAN bus, LAN, WLAN, TCP/IP, Ethernet, Bluetooth.

A control signal is defined in the sense of the present invention as an individual control signal, a control signal as part of a set of control signals, as well as a plurality or a set of control signals.

A data signal is defined in the sense of the present invention as an individual data signal, a data signal as part of a set of data signals, as well as as a plurality or a set of data signals.

An output signal is defined in the sense of the present invention as an individual output signal, an output signal as part of a set of output signals, as well as as a plurality or a set of output signals. A data link is defined in the sense of the present invention as a connection of at least two participants by means of a wired, wireless, optical connection, which is suitable for transmitting output signals, control signals, data signals or output signals. Both direct physical connections (cable connections, radio connections, light guide connections), as well as indirect or logic connections for transmitting information, control signals, data signals or output signals with physical or data technical conversions or transformations of signals, voltages, currents are covered.

A measured gas is defined in the sense of the present invention as a gas or a gas mixture that is such that the at least one gas sensor is sensitive to a change in a gas concentration of this measured gas and responds to changes in the gas concentration of this measured gas with changes in the gas concentration measured value.

A test gas is defined in the sense of the present invention as a gas or a gas mixture that is such that the at least one gas sensor is sensitive to a change in a concentration of this gas or gas mixture and responds to changes in the concentration of this test gas with changes in the gas concentration measured value.

A quantity of a test substance is defined in the sense of the present invention as a quantity of a fluid in the liquid, gaseous or liquid-gaseous phase, which can be converted into a test gas in the sense of the present invention by vaporization, atomization, nebulization, evaporation or by means of a change in pressure, especially by decompression by means of pressure reduction.

The provision of a possibility of checking according to the present invention whether unhindered supply of gas into the gas sensor is given through the at least one gas admission element enables the user, e.g., the maintenance workers, especially in larger industrial plants, to perform the readiness of gas sensors to operate without major personnel expenditure in terms of work time, and hence especially and preferably also routinely.

An unimpeded supply (flow/diffusion) of gas is a basic requirement for an output signal of the gas sensor, which signal is a noncritical gas concentration, a zero (null) signal, i.e., a complete or nearly complete absence of a harmful gas, to be also able to be correctly interpreted by the user as a noncritical situation. A situation in which the zero signal is outputted as an output signal of the gas sensor, even though the at least one gas admission element does not allow unhindered supply of gas (ambient/environmental gas) into the gas sensor, is problematic.

A test gas dispensing unit is therefore arranged according to the present invention downstream of the at least one gas admission element in the gas-measuring arrangement (between the (at least one) gas admission element and a sensor measuring arrangement). The test gas dispensing unit is configured to dispense or to allow to flow a liquid phase, a gaseous phase or a liquid-gaseous phase of a quantity of a test substance from a test substance reserve (container, test substance reservoir or test gas reservoir, tank) to the sensor-measuring arrangement arranged in the gas sensor. The sensor-measuring arrangement is configured to detect a gas concentration or a change in a gas concentration.

A test substance reserve is defined in the sense of the present invention as a container for storing and providing the quantity of test substance, i.e., a fluid in the liquid, gaseous or liquid-gaseous phase. The test substance reserve is configured as a tank test substance reservoir, test gas reservoir, test fluid reservoir or container (cylinder), the quantity of test substance being stocked, stored and made available for dispensing in the test substance reserve by means of the test gas dispensing unit in the gaseous form under pressure or in the liquid state of aggregation under ambient pressure, as well as in a combined liquid/gaseous state, at least partly under pressure, for example, in the form of a liquefied gas cylinder (propane, butane).

The following may be mentioned here as some of the examples for sensor-measuring arrangements in different types of gas sensors:

Electrode/electrolyte combinations in electrochemical gas sensors, radiation source/detector element combinations in infrared optical gas sensors, catalytically active and/or catalytically passive measuring elements in catalytic gas sensors or in heat tone sensors (pellistors), field effect transistors with gas species-sensitive semiconductor elements, for example, gas species-sensitive gate substrates in semiconductor gas sensors.

For example, gas generators or configurations of the test substance reserve or configurations of tank type containers combined with valves, switching means or piezo dispensing elements, which are operated, checked, controlled or regulated by a control unit such that defined quantities of test gas or a defined quantity of test substance can be sent or fed to the gas sensor in the liquid or gaseous form, are suitable configuration possibilities for embodying test gas dispensing units.

A memory for providing predefined durations, measured signal threshold values, comparison criteria or comparison variables are associated with the control unit, or the memory is also contained as an element in the control unit.

For example, dispensing by means of time intervals or durations, whose beginning and end are defined by the control unit, makes it possible to set the quantity of test substance reproducibly and accurately, especially if this quantity of test substance is being stored in the test substance reserve under a defined and known pressure.

The quantity of test substance or the test gas is preferably fed into the gas sensor by means of the test gas dispensing unit in the liquid form, because stocking or storage in the liquid form in the test substance reserve has the advantage of placing, in a relatively small volume, close to the gas sensor, a quantity of test substance that is sufficient for the duration of the use (service life) of the gas sensors. Such a storage is known, for example, from gas lighters, in which butane is used as a liquefied gas. The gas sensor or the gas-measuring arrangement have according to the present invention at least one sensor-measuring arrangement for detecting a gas concentration or a change in a gas concentration. The gas sensor has a suitable configuration by means of the sensor-measuring arrangement and is intended for the qualitative as well as quantitative analysis of gases or gas mixtures fed to this gas sensor from the measuring environment by means of a gas inlet. In addition, the at least one gas admission element, the test gas dispensing unit and the control unit are arranged at or associated with the gas sensor or the gas-measuring device.

The at least one gas admission element is arranged at the gas sensor at the gas inlet or at a gas inlet of the gas-measuring device such that air, gases or gas mixtures from the measuring environment must first pass through the gas admission element to reach the sensor-measuring arrangement in the gas sensor. The feed preferably takes place through the gas admission element by means of diffusion. The at least one gas admission element is configured, for example, as a semipermeable or permeable membrane, a protective grid or a flame protection disk or sintered disk and acts functionally as a diaphragm, as a protection against the entry of contaminants or moisture into the gas sensor, on the one hand, and also as an explosion protection in the embodiment as a flame protection disk. This at least one gas admission element is arranged upstream (with respect to a diffusion flow path) of the sensor-measuring arrangement for carrying out the above-described functional actions.

An embodiment of the gas sensor or of the gas-measuring arrangement or of the gas-measuring device with a plurality of gas admission elements appears, for example, in a constellation/configuration with a plurality of gas sensors in a gas-measuring arrangement or gas-measuring device such that each of the plurality of gas sensors has at least one gas admission element arranged directly at the respective gas inlet of the gas sensor, configured, for example, as a diaphragm, upstream of the respective sensor-measuring arrangement, and, in addition, an additional gas admission element, configured, for example, as a protective grid or flame protection disk, is arranged at a central gas inlet of the gas-measuring arrangement or gas-measuring device.

The test gas dispensing unit may be arranged in such an embodiment according to the present invention both downstream of one of the gas admission elements arranged directly at the respective gas inlet of one of the gas sensors and downstream of the additional gas admission element, i.e., upstream of one of the gas inlets and of the respective corresponding gas admission elements of the gas sensors in the gas-measuring device. The test gas dispensing unit is arranged in both cases in the course of the incoming flow between the gas admission element or gas admission elements and one of the sensor-measuring arrangements in the gas-measuring device. The flow directions—upstream as well as downstream—are defined by the incoming flow of gas from the measuring environment in the direction of the gas sensor or in the direction of the gas-measuring device towards the sensor-measuring arrangements.

The method according to the present invention for testing the at least one gas admission element of the gas sensor or for testing the at least one gas admission element of a gas-measuring device with at least one gas sensor is carried out according to a first aspect of the present invention such that the following actions are carried out from a continuous measuring operation controlled by a control unit in the following sequence of steps:

the control unit brings about the dispensing of a predefined quantity of test substance by means of the test gas dispensing unit arranged downstream of the gas admission element and upstream of the sensor-measuring arrangement to a sensor-measuring arrangement arranged in the gas sensor in the gas sensor, the control unit initiates a continuous detection of a plurality of measured signals of the gas sensor for a predefined detection time and the storage of this plurality of measured signals as a set of measured signals over the predefined detection time in a memory and the storage of corresponding time information in the memory for at least some of the measured signals of the set of measured signals, the control unit determines a maximum of the measured signals and a detection time of the maxima of the measured signals from the set of measured signals, from the set of measured signals over the predefined detection time, the control unit selects, on the basis of the time information, at least one additional measured signal with a detection time that is spaced in time and follows the detection time of the maximum of the measured signals, the control unit compares the at least one additional signal with the maximum of the measured signals, and on the basis of the comparison of the maximum of the measured signals with the at least one additional signal, the control unit determines whether the gas admission element is ready to operate for feeding air, gas or gas mixture from a measuring environment and an indicator of the readiness of the gas sensor to operate and/or the readiness of the gas-measuring arrangement with the at least one gas sensor to operate.

The method according to the present invention makes it possible to perform a testing from the continuous measuring operation in the first operating state at regular time intervals, for example, in a time rhythm, of 24 hours to several days or weeks, which rhythm can be selected in the gas-measuring device or at the gas sensor, to determine whether unhindered supply of gas from the measuring environment is guaranteed to the gas-measuring device or to the gas sensor.

The continuous measuring operation represents, so to speak, the regular operating state of the gas-measuring device as well as the regular operating state of the gas sensor and can be configured as a continuous, ongoing or routine detection of measured signals, a detection of measured signals controlled in time by means of a detection rate (scanning rate), for example, at a detection rate that corresponds to a measured signal detection of a predefined number of measured signals per second or minute, or it may be configured as a measured signal detection in which the detection of a predefined number of measured signals is initiated by an event or by a trigger.

The testing according to the present invention of the supply from the measuring environment or the permeability to gas of the gas admission element represents according to the present invention only an interruption of the continuous measuring operation for a short time of usually less than one minute.

The predefined quantity of test substance is dispensed downstream of the gas admission element and upstream of the sensor-measuring arrangement, i.e., at a site that is located between the gas admission element and the sensor-measuring arrangement. Thus, the dispensing takes place in the interior of the gas sensor. The quantity of test substance dispensed in the interior at this site reaches as a test gas, as an incoming test gas flow, the sensor-measuring arrangement, and in case the gas admission element is permeable to the test gas being dispensed, it enters the measuring environment through the gas admission element as a test gas outflow, i.e., it flows out of the gas sensor. The duration, starting with the dispensing of the quantity of test substance or starting with the inflow of test gas to the sensor-measuring arrangement, which corresponds to the sum of the duration of the test substance inflow to the sensor-measuring arrangement and of the test substance outflow into the measuring environment, is called the process time.

The detection of a plurality of measured signals is brought about, prompted or initiated by the control unit for a predefined time after the dispensing of the quantity of test substance, and storage of corresponding time information concerning the detection in the memory is brought about, prompted or initiated by the control unit for at least some of the set or plurality of the measured signals. The time information is information that is also called time stamp and contains, indicates or represents information concerning the detection or concerning the detection time of the measured signals. The duration of the predefined detection time comprises at least one process time. This is necessary for the control unit to have available as a set of measured signals for the analysis a signal rise of the measured signals as an effect of the dispensing with the formation of the maximum of the measured signal at a time in the signal pattern and the signal decay of the measured signals following this time in case of unhindered outflow into the measuring environment through the gas admission element. A measured signal, whose detection time is spaced in time and follows the detection time of the maximum of the measured signal, is determined and used by the control unit as the at least one additional measured signal during this analysis. The selected additional measured signal is preferably distanced from the time of the maximum of the measured signals by a predefined duration, such that a time characteristic of the unhindered outflow into the measuring environment, which characteristic is typical of the gas sensor or/and the gas admission element, is taken into account (the time gap of the selected additional measured signal from the time of the maximum of the measured signal is a function of the time characteristic of the unhindered outflow into the measuring environment of the particular gas sensor or/and the gas admission element). A predefined duration that can be applied in practice—assuming free diffusion through the gas admission element from the gas sensor back into the measuring environment, is, for example, a duration after which a drop of the measured signal to about 50% of the maximum can be expected for a gas sensor that is able to function.

The control unit compares the at least one additional measured signal with the maximum of the measured signals and determines on the basis of this comparison whether the gas admission element is ready to function for feeding air, gas or gas mixture from the measuring environment. The control unit can carry out this comparison, for example, by forming a difference or quotient from the maximum of the measured signals and the at least one measured signal. One example of forming a quotient is configured such that if the at least one additional measured signal drops below a certain percentage, for example, 90% of the maximum, a gas exchange with the measuring environment is possible and the gas admission element is therefore ready to function for feeding air, gas or gas mixture from the measuring environment. An example of forming a difference is configured such that if the at least one additional measured signal has a certain, predefined signal difference from the maximum, a gas exchange is possible with the measuring environment and the gas admission element is therefore ready to function for feeding air, gas or gas mixture from the measuring environment. Based on the above-described comparison, the control unit determines an indicator of the readiness of the gas sensor and/or of the gas-measuring arrangement with at least one gas sensor to operate.

In a preferred embodiment, the control unit can take into account, for example, the size and/or the volume of the gas sensor, as well as the number of the gas admission elements, the thickness, pore size, area and/or diameter of the respective gas admission element for the duration of the predefined time. This leads to the advantage that the configuration of the gas sensor can thus also be included in the testing of the gas admission element, so that the gas admission element can be tested in a more specific manner. The number of gas admission elements, and the thickness, area or diameter, and pore size of the gas admission element determine the rate of the gas supply by diffusion as well as of the gas discharge by diffusion.

Provisions are made in a special embodiment for the gas-measuring device or the gas sensor to provide a substitute signal for the duration of the interruption. This is used to avoid possible misinterpretations of the measured signal on a display element or at a data interface, for example, in the form of the triggering of a gas concentration alarm. Such a substitute signal may be, for example, a chronologically preceding measured signal or a signal that is derived from one or a plurality of chronologically preceding measured signals and which is provided by means of an output unit. However, a status signal, which indicates for the duration of the testing of the gas admission element that the gas-measuring device or the gas sensor is not currently ready for measuring gases from the measuring environment, may also be provided as a substitute signal by the output unit.

In a preferred embodiment, the dispensing of the quantity of test substance is brought about as dispensing in the form of a quantity of liquid test substance. This quantity of test substance dispensed in the liquid form then changes over from the liquid phase into the gaseous phase in the gas sensor after the dispensing at a time $t_1$, for example, due to evaporation or due to atomization brought about by impingement on a wall arranged in/at the gas sensor and is available in the gas sensor as a quantity of gaseous test substance at the sensor-measuring arrangement at a time $t_1'$. This quantity of gaseous test substance brings about a reaction of the sensor-measuring arrangement in the gas sensor in the form of a change in the gas concentration measured value as a measured signal or output signal.

If the gas sensor is configured, for example, as an electrochemical gas sensor, there will be a change in the output signal in/at the sensor-measuring arrangement based on chemical and/or electrochemical reactions.

If the gas sensor is configured, for example, as an infrared optical gas sensor with a measuring cuvette, there will be an attenuation of the propagation of light in the measuring cuvette to the sensor-measuring arrangement and a change in the output signal in a wavelength range of the optical gas sensor due to the absorption properties of the test substance.

If the gas sensor is configured, for example, as a catalytic gas sensor, there will be a change in the output signal based on combustion reactions and/or chemical reactions at the measuring element (pellistor) as a sensor-measuring arrangement with the quantity of gas test substance.

If the gas sensor is configured, for example, as a semiconductor gas sensor, there will be a change in the output signal based on chemical reactions at the gas species-specific semiconductor elements of the sensor-measuring arrangement.

In a preferred embodiment, the dispensing of the predefined quantity of test substance from the test gas dispensing unit to the sensor-measuring arrangement in the gas sensor is brought about by the control unit such that the test gas dispensing unit is activated at a first time (activation time) $t_1$. It is achieved due to the configuration of the test gas dispensing unit that a quantity of test substance of an exactly defined quantity or volume is dispensed with the activation at the first time (activation time) $t_1$, without deactivation of the test gas dispensing unit by the control unit being necessary. A configuration that can make possible the dispensing of a quantity in the described type of this configuration can be embodied, for example, by a piezo dispensing element. Such a piezo dispensing element is configured to dispense an exactly defined quantity of test substance upon a single-time activation. A piezo dispensing element operates according to the piezoelectric effect, in which a deformation is brought about in the piezo material, for example, ceramic, in case of activation by an electrical voltage pulse. An extrusion pressure corresponding to this deformation results from the deformation. The defined quantity of test substance is dispensed with the extrusion pressure through a fine nozzle. The use of such piezo elements, or piezo ceramic dispensing elements, is known, for example, from the field of printing technology (ink jet printers) as so-called ink jet technology.

In a preferred embodiment, the dispensing of the predefined quantity of test substance by the test gas dispensing unit to the sensor-measuring arrangement in the gas sensor is brought about by the control unit such that the test gas dispensing unit is activated at a first time (activation time) $t_1$ and deactivated at a second time (deactivation time) $t_2$.

The test gas dispensing unit dispenses a quantity of liquid test substance, which is indirectly predefined by the time interval, to the sensor-measuring arrangement in the gas sensor. The second time (deactivation time) $t_2$ is obtained as a time spaced in time from the first time (activation time) $t_1$ by a deactivation of the test gas dispensing unit by means of the control unit. A configuration with activation and deactivation is ideal and practicable, for example, in advantageous embodiments of electrical switching signals in conjunction with the test gas dispensing unit with one or more electrically controlled valves.

The predefined quantity of test substance is determined by the predefined time interval in conjunction with the predefined general conditions, such as the pressure prevailing in the test substance reserve, the temperature and an opening cross section of a valve used for the activation and deactivation. Such a predefined quantity of liquid test substance is also called bolus or bolus quantity. Many different types of valves that can be used for dispensing fluids or liquids, such as digital on-off valves with binary states (normally open [NO] or normally closed [NC]) or also proportional valves may be used as valves in the test gas dispensing unit. Another configuration with activation and deactivation is practicable, for example, in the form of electrical setting signals for gas generation by means of one or more gas generators as a test gas dispensing unit.

A size and/or a volume of the gas sensor is taken into account by the control unit in a special embodiment for the determination of the second time (deactivation time) $t_2$ in the time course t (the deactivation time is a function of the size and/or a volume of the gas sensor). Taking the size and/or the volume of the gas sensor into account makes it possible to take into account different sizes or volumes of gas sensors, which lead to different inflow conditions and inflow quantities. A quantity of test substance that is adapted to the size and the volume can be dispensed in this manner by the test gas dispensing unit by means of the control unit by selecting the second time (deactivation time) $t_2$.

In another preferred embodiment, a size and/or volume of the gas sensor is taken into account by the control unit when determining the portion of the liquid test substance by means of the test gas dispensing unit as well as when dispensing the portion of liquid test substance (the portion of the liquid test substance is a function of the size and/or volume of the gas sensor). The portion of the liquid test substance is correspondingly adapted in this embodiment to the size and/or the volume of the gas sensor, and an adapted bolus of the quantity of test substance, which corresponds to the size and/or the volume of the gas sensor, is determined by the control unit and dispensed by means of the test gas dispensing unit.

In another preferred embodiment, a status signal is determined and/or provided by the control unit on the basis of the comparison of the at least one additional measured signal with the maximum of the measured signals or with the indicator of the readiness of the gas sensor and/or of the gas-measuring arrangement with the at least one gas sensor to operate. The comparison yields the result showing whether the dispensed quantity of test substance flows or diffuses out of the gas sensor through the gas admission element during the time course—as well as in the corresponding signal pattern of the measured signals—of the process time. If the diffusion from the gas sensor or the outflow from the gas sensor has not taken place by the time of the at least one additional measured signal, a status signal, which indicates that the gas sensor or the gas-measuring arrangement is not able to function correctly, can be generated by the control unit. It can be determined from the situation that a dispensed quantity of test substance has not left, as expected, the gas sensor through the gas admission element that the inflow from the measuring environment into the gas sensor through the gas admission element is not optimal, either or may even be impossible due to a blockage.

In another preferred embodiment, the status signal is provided by the control unit for the output unit, a central analysis system, a central alarm unit or a mobile output device. Such provision for an output unit, a central analysis system, a central alarm unit or a mobile output device, for example, a mobile telephone or another mobile communication device, makes it possible to communicate the status of the gas sensor or of the gas-measuring arrangement to additional external locations. Suitable data links or data transmission devices (0-10 V, 4-20 mA, Ethernet, LAN, W-LAN, USB, RS232, etc.) are provided for this purpose for connecting the control unit to the output unit as well as to the central analysis system or to the central alarm unit or to the mobile output devices. The data links are configured to transmit measured data as well as gas concentration values, alarm signals or also unwanted signals to the output unit, the central analysis system, the central alarm unit or mobile output devices.

An alarm signal or a message is outputted by the output unit, the central analysis system, the central alarm unit or the mobile output devices in another embodiment.

In another preferred embodiment, the alarm signal is provided by the control unit and/or the output unit for an acoustic alarm generator for generating an acoustic alarm and/or for an optical signal generator for generating an optical or visual, visible alarm.

In another preferred embodiment, the message provided is provided by the control unit and/or the output unit in a visible form on a display unit, a screen or another device suitable for visualization as an instruction, especially as a warning message or as an instruction in text form, graphic form or symbolic form.

The embodiments described represent, both in themselves and combined with one another, special embodiments of the method according to the present invention for testing the gas sensor or the gas-measuring device, especially the gas admission element. Advantages and additional embodiments arising through a combination or combinations of a plurality of embodiments are likewise covered by the inventive idea, even though not all possibilities of combining embodiments for this are explained in detail. The above-described embodiments of the method may also be configured in the form of a computer-implemented method as a computer program product with a computer, in which case the computer is prompted to execute the above-described method according to the present invention when the computer program or parts of the computer program are executed on the computer or on a processor of the computer or on a so-called "embedded system" as part of a gas-measuring device, gas sensor or gas-measuring arrangement or on a—preferably computer-assisted—analysis system associated with the gas sensor or the gas-measuring arrangement. The computer program may also be stored on a machine-readable storage medium. In an alternative embodiment, it is possible to provide a storage medium that is intended for storing the above-described, computer-implemented method and can be read by a computer. It is within the scope of the present invention that all the steps of the method or of the computer program do not necessarily have to be executed on one and the same computer, but they may also be executed on different computers. The sequence of the method steps may possibly be varied as well.

The accomplishment of the object was described above with reference to the method claimed as the first aspect of the present invention. Features, advantages or alternative embodiments mentioned in this connection may likewise be extrapolated to the subjects claimed according to another aspect of the present invention and vice versa. The corresponding functional features of the method may be configured according to the invention by corresponding physical modules or units of a device, especially by hardware components (µX, DSP, MP, FPGA, ASIC, GAL), which may be implemented, for example, in the form of a processor, a plurality of processors (µX, µP, DSP) or in the form of instructions in a memory area, which are processed by the processor.

Another aspect of the present invention thus arises, which accomplishes the objects set according to the present invention by a device for carrying out the method for testing a gas sensor and by a gas-measuring device with a testing device for testing the gas sensor. This device, suitable for carrying out the method, is configured such that the testing of the gas sensor and/or of the gas-measuring device or gas-measuring arrangement is carried out according to the steps described in the method and the additional steps described in the embodiments are also carried out each in itself or combined.

The gas-measuring device according to the present invention with a testing device for carrying out the method has for this at least one gas sensor with a gas admission element, with at least one sensor-measuring arrangement, with a test gas dispensing unit, a control unit and a memory associated with the control unit. The processing and the control of the operating states are carried out by means of the control unit. The measured signal detection, the control of dispensing, the storage of measured signals, the comparisons of the measured signals with threshold values and the determination of the indicator of the readiness of the gas sensor to operate are controlled by the control unit in conjunction with the memory. The gas admission element is arranged upstream of the sensor-measuring arrangement in the gas sensor or in the gas-measuring arrangement, and the test gas dispensing unit is arranged downstream of the gas admission element in the gas sensor or in the gas-measuring arrangement.

In one embodiment, the test gas dispensing unit is configured as a piezo dispensing element and a reservoir fluidically connected to the piezo dispensing element. The reservoir, for example, in the form of a tank, is configured for stocking a test substance reserve. The control unit is configured to activate the piezo dispensing element at a first time $t_1$ in order to bring about the dispensing of a quantity of test substance, which is being stocked in the test substance reserve, to the gas sensor or to the gas-measuring arrangement.

In a preferred embodiment, the test gas dispensing unit is configured by a valve in conjunction with a reservoir fluidically connected to the valve. The reservoir is configured, for example, as a tank for storing or stocking a test substance reserve. The control unit is configured to bring about an activation of the valve at a first time $t_1$ and a deactivation of the valve at a second time $t_2$ in order to bring about the dispensing of a quantity of test substance from the test substance reserve to the gas sensor or to the gas-measuring arrangement. As a result, the activation and deactivation preferably take place by means of electrical switching signals, which can be transmitted by the control unit to the test gas dispensing unit.

In an especially preferred embodiment, the gas-measuring device has an output unit, an optical alarm generator or an acoustic alarm generator. The optical alarm generator and/or the acoustic alarm generator are configured and provided, in cooperation with the control unit and/or with the output unit, to output an alarm signal. The gas-measuring device additionally has here an optical interface, which is configured and provided in cooperation with the control unit to transmit a status signal to an analysis system.

In another preferred embodiment, the sensor-measuring arrangement is configured as a combination of electrodes and an electrolyte in an electrochemical gas sensor, as a combination of a radiation source and of a detector element in an infrared optical gas sensor, as a combination of catalytically active and/or catalytically passive measuring elements in a catalytic gas sensor, or in a heat tone sensor, as well as as gas species-specific and sensitive semiconductor elements in a semiconductor gas sensor.

With the method for testing a gas sensor and with the gas-measuring device with a testing device for testing a gas sensor, the present invention provides an advantageous possibility, which can technically very easily be embodied, for the reliable determination of whether an unhindered supply of gas is possible through the gas admission element into the gas-measuring device or to the gas sensor.

In addition, another advantage is that it is also possible to test the function of the gas sensor itself, as well as the dispensing of the quantity of test substance proper by means of the method of dispensing the predefined quantity of test substance. This arises from the fact that the measured signal shows no change even if either the sensor-measuring elements in the gas sensor do not function as intended or are defective, or if the dispensing of the predefined quantity of test substance does not function properly. This leads to the advantage that in addition to the testing of the gas admission elements belonging to the gas sensor or the gas-measuring device, it is possible to test both the testing device with the function of dispensing the quantity of test substance proper and the function of the gas sensor or of the gas-measuring device or of the sensor-measuring elements and elements for signal processing with the method for testing a gas sensor and with the gas-measuring device with a testing device for testing a gas sensor. This leads, on the whole, to the advantage that no possible situation, in which a malfunction of one or more of the essential components of the gas sensor or of the gas-measuring arrangement with a gas sensor, i.e., gas admission element or the sensor-measuring elements, as well as of the elements (supply lines, electronic units, amplifiers, A/D converters) for signal processing, which components and elements are essential for a reliable, safe and high-quality operation, will essentially remain unnoticed.

A special advantage arises additionally, namely, that it is also possible to detect a possible malfunction of the test gas dispensing unit, for example, a possible blockage or leakage during the feed of the quantity of test substance or of the valve provided for dispensing, a disturbance in the electrical control of the valve (e.g., signal error, line break, broken wire) or an empty test substance reserve. These causes of error cannot be differentiated and distinguished from one another in all cases, and the advantage arises for the use that arrangements for gas measurement and gas sensors that are able to function can be clearly distinguished from malfunctioning devices and gas sensors.

The present invention will be explained in more detail by means of the following figures and the corresponding descriptions of the figures without limiting the general inventive idea. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
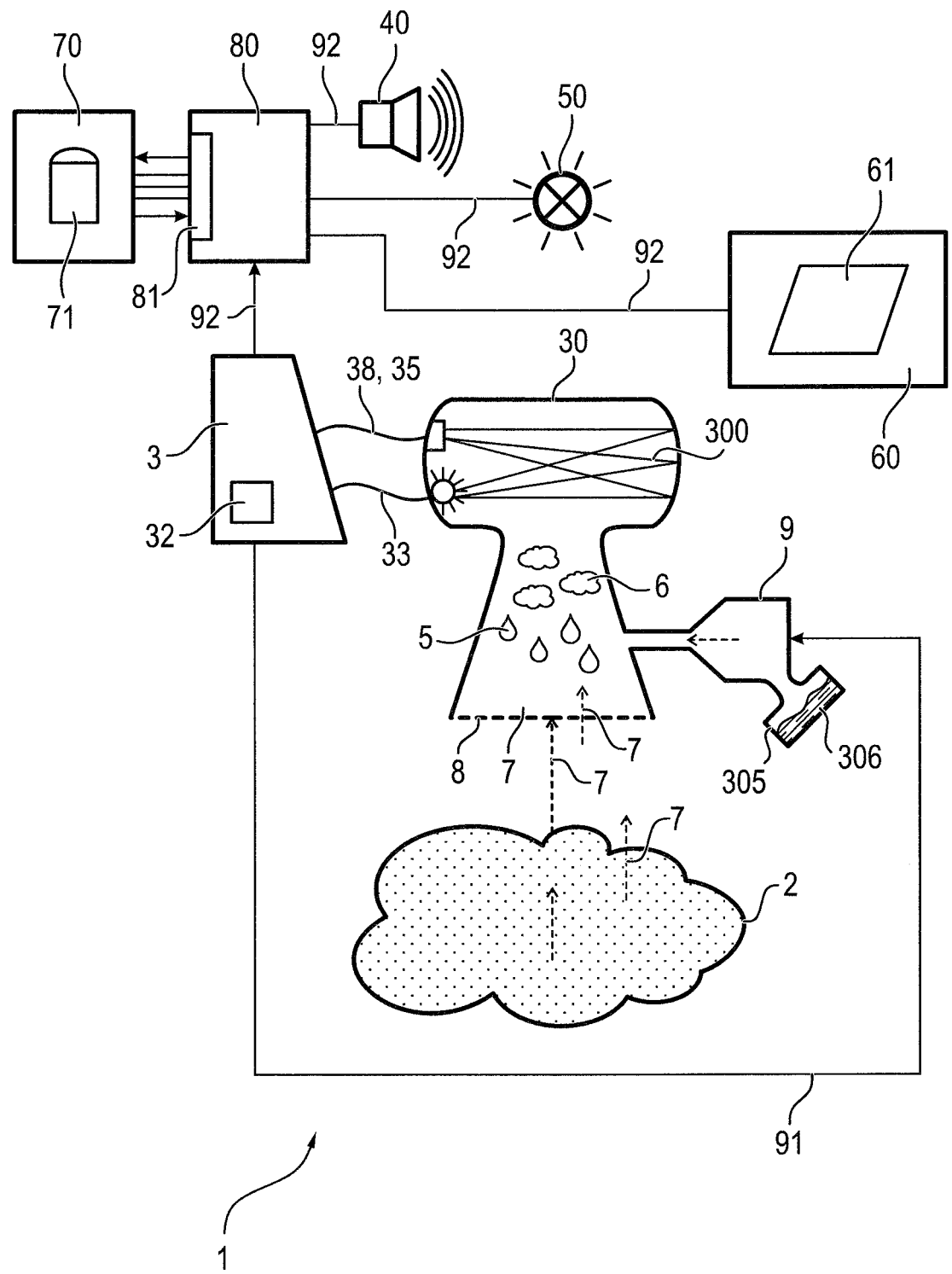
FIG. 1a is a schematic view showing a gas-measuring arrangement with an optical gas sensor and with a testing device.
Figure 1B:
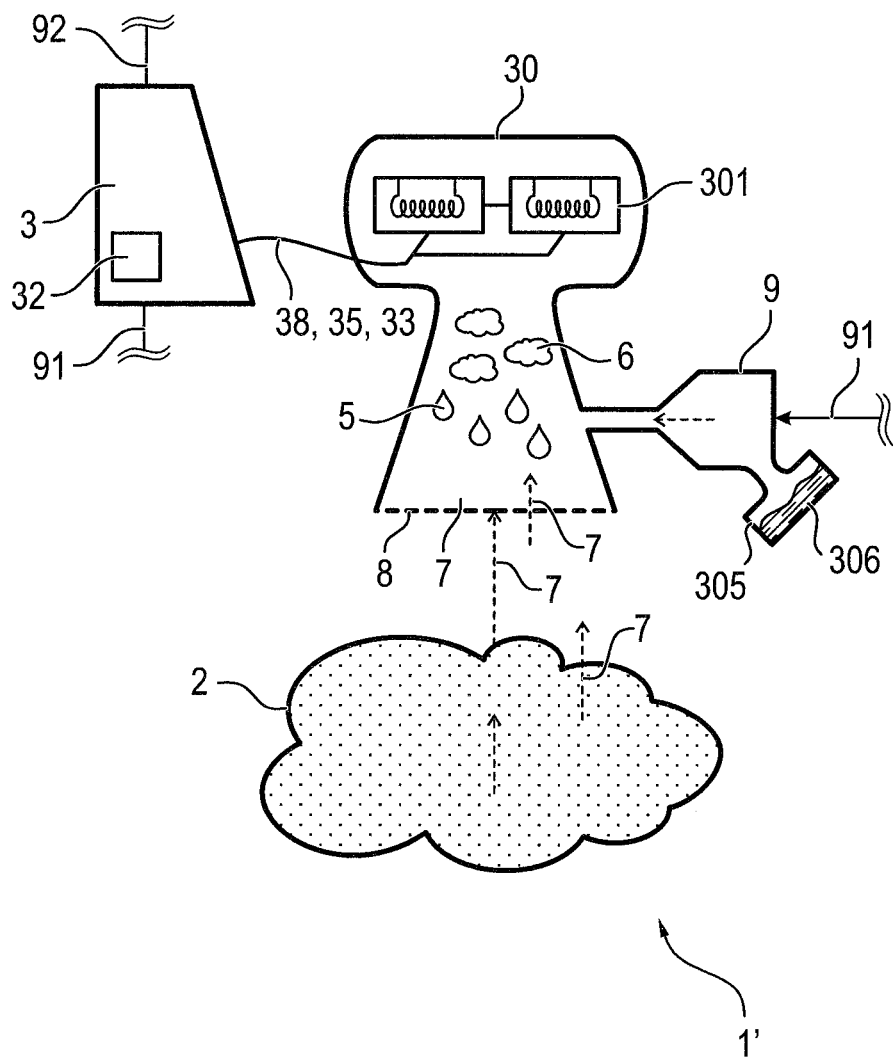
FIG. 1b is a schematic view showing a gas-measuring arrangement with a catalytic gas sensor and with a testing device.
Figure 1C:
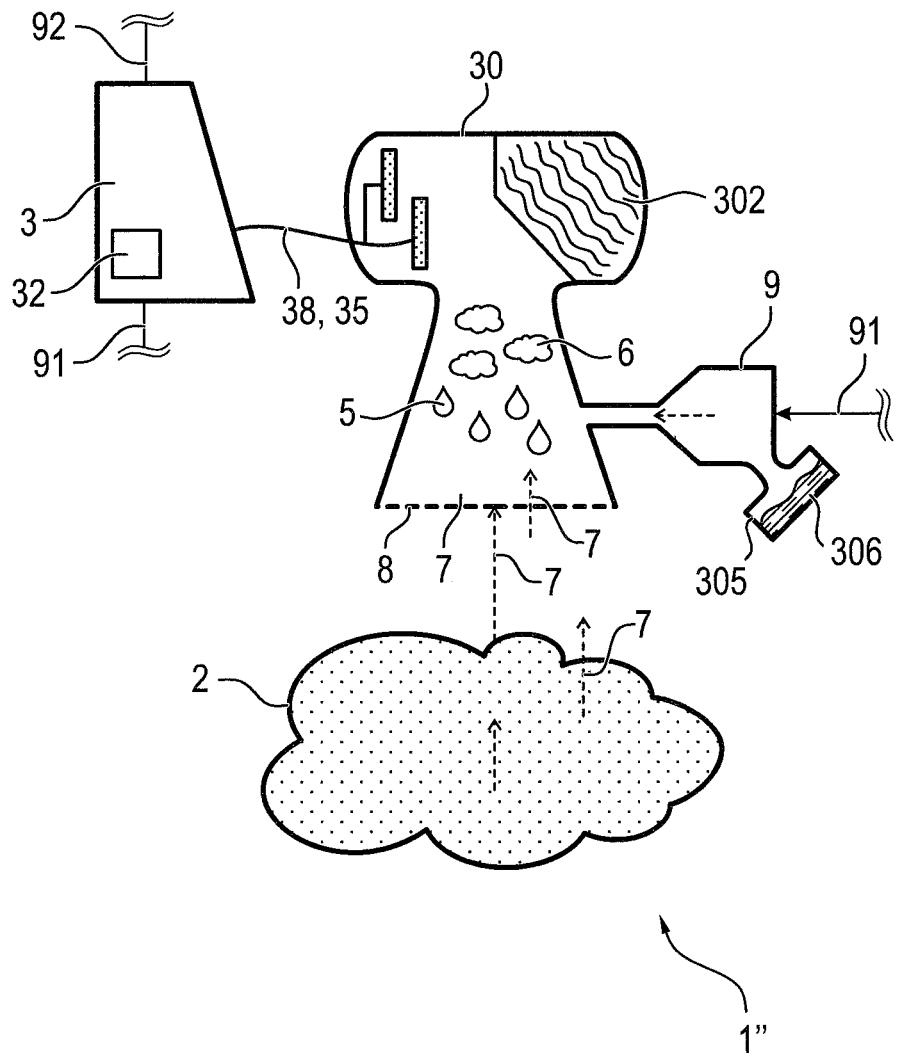
FIG. 1c is a schematic view showing a gas-measuring arrangement with an electrochemical gas sensor and with a testing device.

Referring to the drawings, FIGS. 1a, 1b, 1c as well as 1d show arrangements for gas measurement with a gas sensor and with a testing device. FIG. 1a shows a gas-measuring arrangement 1 with an optical gas sensor 300. The optical gas sensor 300 is configured as a cuvette with a multireflection cell, not shown in detail in this FIG. 1a for reasons of clarity. A radiation source and a detector element are arranged as a sensor-measuring arrangement in the multireflection cell. Light is radiated in the multireflection cell from the radiation source onto an opposite wall as well as to side walls, reflected from there and detected by the element after multiple reflections. The presence of a test gas to be measured, for example, methane, ethane, butane, propane, changes the absorption for the emitted light in the infrared wavelength range. This can be detected as a measurement effect of an attenuated signal on the detector element. The measurement effect of an attenuation of the emitted IR light by certain gases, for example, methane, ethane, butane, propane, and other hydrocarbons is thus obtained. The gas from a measuring environment 2 enters the optical gas sensor 300 via a gas admission element 8, for example, a semipermeable or permeable diaphragm, a protective grid or a flame protection disk, entering the measuring cuvette of the optical gas sensor 300. Only a single gas admission element 8 is shown in this FIG. 1a as an embodiment of the environmental/ambient gas supply 7 with a gas admission element 8.

Figure 1D:
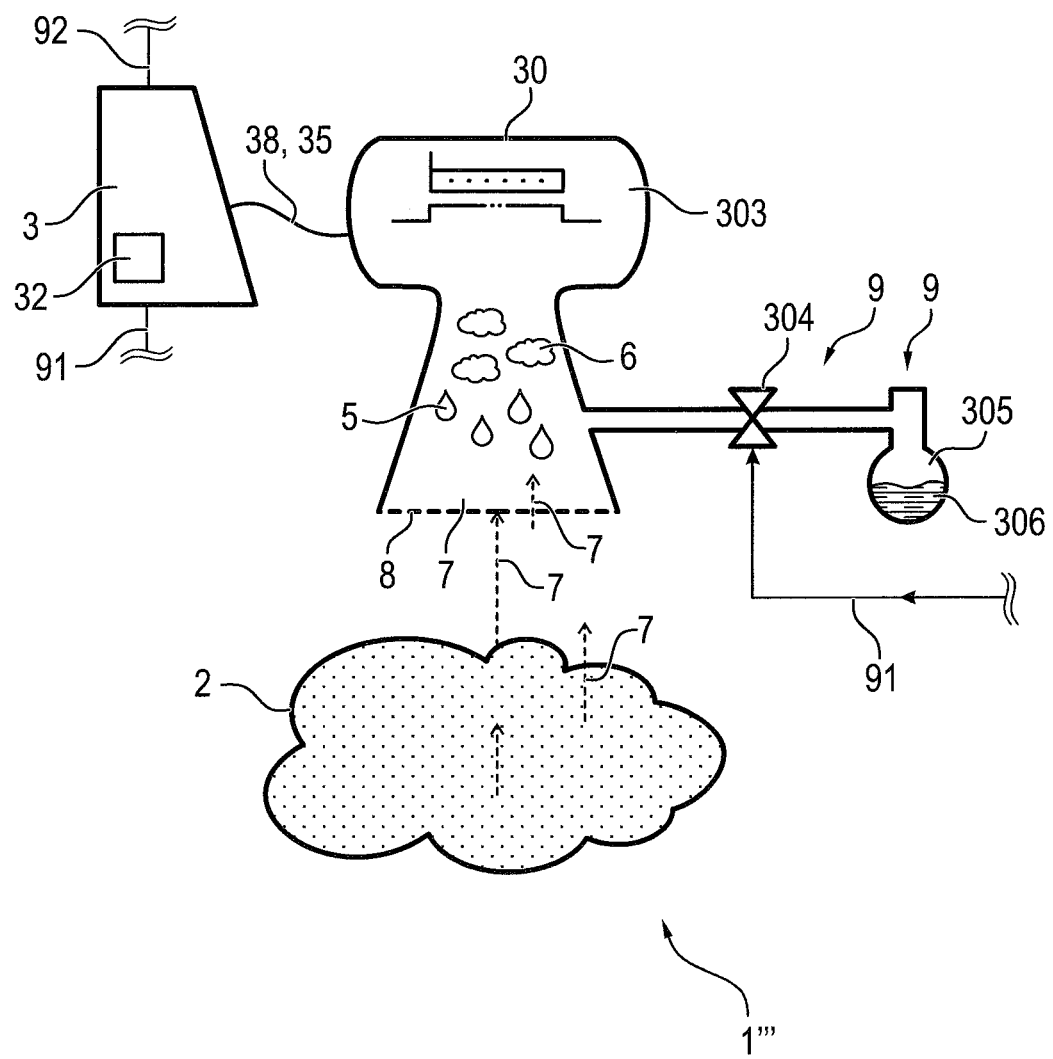
FIG. 1d is a schematic view showing a gas-measuring arrangement with a semiconductor gas sensor.

In an embodiment of a gas-measuring arrangement 1 in a device in which a plurality of gas sensors are arranged as a gas sensor system 30, it is technically common and advantageous in many technical embodiments to provide a plurality of gas admission elements 8 arranged one after another in a row. It is thus conceivable that, downstream from the measuring environment 2, a first gas admission element acts as a flame protector or dust protector, followed by a second element preventing the entry of moisture and a third element 8 in the gas sensor proper protects, for example, the optical gas sensor 300 or a catalytic gas sensor 301 (FIG. 1*b*) or an electrochemical gas sensor 302 (FIG. 1*c*) or a semiconductor gas sensor 303 (FIG. 1*d*). The test gas dispensing unit 9 may be arranged both downstream of the measurement between the first and second gas admission elements, between the second and third gas admission elements 8 or between the third gas admission element 8 and the gas sensor system 30, 300. These embodiments with a plurality of gas admission elements and possible, suitable positions in which the test gas dispensing unit 9 is arranged are not shown in the gas-measuring arrangement 1 for the sake of clarity of this FIG. 1*a*. However, these possible embodiments are also covered in the sense of the present invention as arrangements of the test gas dispensing unit 9 at the gas sensor system 30. Such a gas supply (supply of environmental/ambient gas) 7 takes place from the measuring environment 2 towards the optical gas sensor 300.

A test gas dispensing unit 9 is arranged at the optical gas sensor 300 downstream of the gas admission element 8 in this gas-measuring arrangement 1 according to FIG. 1*a*. A quantity of liquid test substance 5 is dispensed by this test gas dispensing unit 9 from a test substance reserve 305, for example, from a tank 305 containing a reserve quantity 306. This quantity of test substance 5, injected in the liquid form, vaporizes, is atomized or evaporates in the gas sensor 300 to form a quantity of gaseous test substance 6, which is then located in the optical gas sensor 300 for the measurement. The test gas dispensing unit 9 is actuated by means of a control line 91 by a control unit 3 such that a predefined quantity of liquid test substance 5 is dispensed into the optical gas sensor 300 upstream of the gas admission element 8 at predefined times $t_1$. In a preferred variant, the test gas dispensing unit 9 is configured as a piezo dispensing element. Such a piezo dispensing element is configured, combined with the test substance reserve 305, to dispense an exactly defined quantity of test substance each upon a single-time activation by means of a control signal 91' (FIG. 2), without deactivation of the piezo dispensing element, for example, by an additional control signal 91" (FIG. 2) or by an exactly defined duration of the control signal 91" (FIGS. 2, 3), thus defined by a time control 44 (FIG. 3), being necessary.

The control unit 3 receives measured signals 35, 38 from the optical gas sensor 300 and from the detector element in the optical gas sensor 300. Furthermore, the control unit 3 controls the infrared optical radiator in the optical gas sensor 300 by means of a control line 33. The measured signal 35, as well as a measured signal pattern 38 based on the measured signal 35 are transmitted by the control unit 3 to an output unit 80 by means of a data or signal line 92. The output unit 80 is configured to actuate an acoustic alarm generator, for example, a horn 40, or an optical alarm generator, for example, a lamp 50, by means of the signal and data line 92. Furthermore, the output unit 80 is configured by means of an interface 81 to transmit data, analysis results, sensor signals, data signals or processed measured signals 35, 38 to an analysis system 70 via signal and data lines 92 as well as control lines 91. A data bank 71, which can log states and events of tests of the gas-measuring arrangement 1, is preferably arranged in the analysis system 70. An operating and display unit (user interface) 60 is connected by the output unit 80 via a signal and data line 92. The operating and display unit 60 has a display screen 61, on which error messages as well as instructions for a user, as well as measured signals or measured values can be displayed. The control unit 3 and the test gas dispensing unit 9 cooperate in conjunction with a memory 32 arranged in the control unit 3 or with a memory 32 associated with the control unit 3 in a method for testing the gas-measuring arrangement 1, as is explained in more detail in FIGS. 2 and 3. The response of the optical gas sensor 300 to the dispensing of a quantity of liquid test substance 5 with evaporation of the quantity of liquid test substance 5 into a quantity of gaseous test substance 6 into the optical gas sensor 300 is used to check the time during which this dispensed quantity of test substance 5 diffuses again from the optical gas sensor 300 via the gas admission element 8. It is determined for this by the control unit 3 on the basis of detected measured signals with respect to a maximum of the measured signals whether the dispensed quantity 5, 6 has escaped from the optical gas sensor 300 after a certain time or not. If this dispensed quantity of test substance 5, 6 has not escaped from the optical gas sensor 300 after a predefined time, it can be inferred or determined by the control unit 3 that an incorrect situation is occurring at the gas admission element 8.

FIG. 1*b* shows a modified gas-measuring arrangement 1' compared to FIG. 1*a*. Instead of the optical gas sensor with an infrared multireflection cell 300, a catalytic gas sensor 301 is shown in FIG. 1*b*. Such a catalytic gas sensor 301, also known as heat tone sensor, is connected to a control unit 3 and to a test gas dispensing unit 9, similarly to what is described in FIG. 1*a* in connection with the optical gas sensor 300. Identical elements in FIGS. 1*a* and 1*b* are designated by the same reference numbers in FIGS. 1*a* and 1*b*.

The description of the functionality and the interaction of the control unit 3 with the test gas dispensing unit 9 can also be extrapolated, as is explained in connection with FIG. 1*a*, to the functionality of the interaction of the control unit 3 and the catalytic gas sensor 301 with inclusion of the test gas dispensing unit 9 for testing the gas admission element 8.

The elements shown in FIG. 1*a*, namely, the output unit 80, the analysis system 70 and the operating and display unit 60 with the corresponding additional elements, as well as the data lines 92, as well as control lines 91 are not shown in detail in FIG. 1*b*. It is, however, implied in the sense of the present invention that the gas-measuring arrangement 1' can interact with the analysis system 70, the analysis unit 80 and the operating and display unit 60 in a similar manner as is described in connection with FIG. 1*a* concerning the gas-measuring arrangement 1. The control lines 91 and data lines 92 are indicated schematically in a simplified manner only in this gas-measuring arrangement 1'.

Unlike in FIG. 1*a* with the gas-measuring arrangement 1, this gas-measuring arrangement 1' shown in FIG. 1*b* shows the aspect that another gas sensor system 30, configured as one or two catalytic measuring elements as a sensor-measuring arrangement, is arranged in the catalytic gas sensor 201, and if a special gas, for example, ethane, methane, butane or propane is fed, these elements engage in a chemical reaction with this gas. A part of the gas is consumed during this reaction at the catalytic measuring elements. This has the effect that a dispensed quantity of test substance 5, 6 will not escape completely into the measuring environment 2 after a predefined time through the gas admission element 8, but there is a shortage, which is due to the consumption of measured gas by the catalytically active measuring elements in the catalytic gas sensor 301. This effect is to be taken into account when testing the gas-measuring arrangement 1' or when testing the gas admission element 8 by means of the quantities of test substance 5, 6 entering by dispensing or diffusion and the escaping quantities of gas after a certain time. This is explained in more detail in FIG. 2 and the corresponding description.

FIG. 1c shows a gas-measuring arrangement 1" with an electrochemical gas sensor 302. Elements that are identical in FIGS. 1a, 1b, and 1c are designated by the same reference numbers in FIGS. 1a, 1b, and 1c. Unlike in FIG. 1a with the gas-measuring arrangement 1, the gas-measuring arrangement 1" in this FIG. 1c shows the aspect that another gas sensor system 30, configured as a sensor-measuring arrangement, preferably comprising a liquid electrolyte and an arrangement of electrodes in the electrochemical gas sensor 302, is arranged. An electrochemical reaction or chemical reaction tales place at the electrodes when feeding a special gas, for example, ammonia. The gas-measuring arrangement 1" is shown in a similarly simplified manner as the gas-measuring arrangement 1' according to FIG. 1b. Comments made in connection with this simplified view in the description of FIG. 1a can also be extrapolated to this FIG. 1c. It should be noted concerning the interaction of the control unit 3 with the test gas dispensing unit 9 and with the electrochemical gas sensor 302 that a gas sensor system 30 with an electrochemical gas sensor 302 also consumes a certain quantity of test gas during the measurement, similarly to a catalytic gas sensor 301 according to FIG. 1b, due to the chemical reaction taking place at the electrodes. This should also be taken into account in this embodiment according to FIG. 1c when testing and setting up the balance of the dispensed quantities of test substance 5, 6 and the quantities of gas escaping through the gas admission element 8. This is described in more detail in FIG. 2 as well as in the description of FIG. 2.

FIG. 1d shows a gas-measuring arrangement 1'''. This gas-measuring arrangement 1''' has a semiconductor sensor 303 as a gas sensor system 30. The explanations given in connection with FIGS. 1a, 1b, and 1c are correspondingly also applicable to FIG. 1d. The gas-measuring arrangement 1''' is explained in a simplified view comparable to FIGS. 1b and 1c. Identical elements in FIGS. 1a, 1b, 1c and 1d are designated by the same reference numbers in FIGS. 1a, 1b, 1c and 1d. The semiconductor sensor 303 is shown in FIG. 1d as a gas sensor system 30. The test gas dispensing unit 9 is shown as an interaction of a test substance reserve 305 with a valve 304 as another difference. This valve 304 is actuated by means of the control line 91 by the control unit 3. Similarly to what was described before in connection with FIGS. 1a, 1b, 1c, a reserve quantity 306 is contained in the test substance reserve 305. The reserve quantity 306 in this FIG. 1d is preferably a liquid gas, which is contained under pressure in the test substance reserve 305. When the valve 304 is opened for a predefined time, a portion of the reserve quantity 306 can enter the semiconductor sensor 303 from the test substance reserve 305. Depending on the value of the overpressure in the test substance reserve 305, a portion of the reserve quantity 306 enters the semiconductor sensor 303 as a quantity of liquid test substance 305 or as a quantity of already evaporated test substance 6. The transition from the liquid phase of the quantity of test substance 5 to the gaseous phase of the quantity of test substance 6 may take place directly due to pressure release when opening the valve 304, as well as when the quantity of liquid test substance 5 impinges on or impacts the walls of the semiconductor sensor 303. The interaction of the control unit 3 with the test gas dispensing unit 9 and the valve 304 and the test substance reserve 305 is described in detail in the description of FIG. 2 as well as in the process shown in FIG. 3 and in the corresponding description of the process according to FIG. 3.

Figure 2:
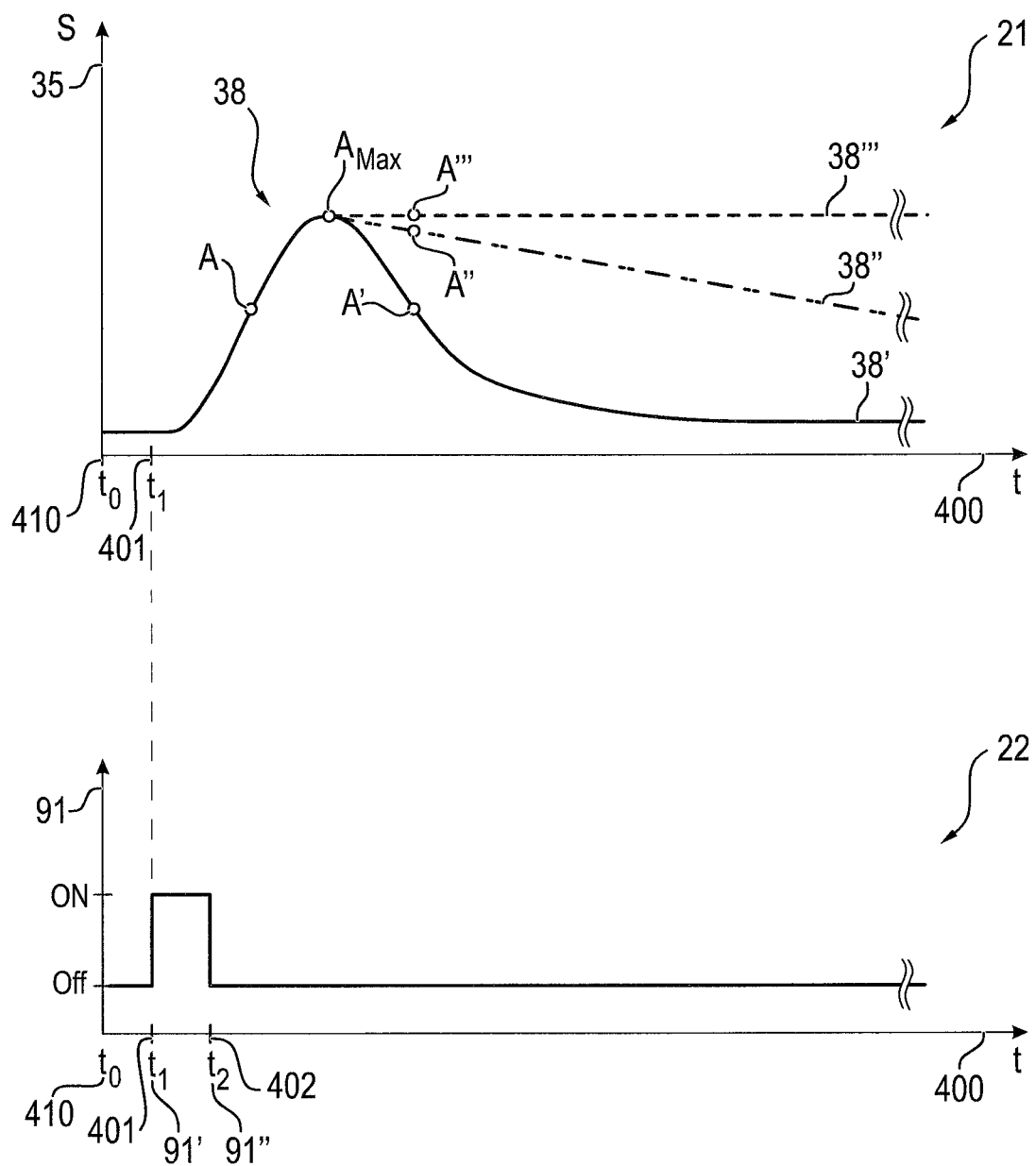
FIG. 2 is a graph of a typical course of a measured signal of a gas sensor during a testing with the testing device.

FIG. 2 shows a typical pattern of a measured signal of a gas-measuring arrangement with a gas sensor during a testing with a testing device. Three diagrams 21, 22 are shown, which represent each a time curve t 400 synchronized with one another.

A measured signal pattern 38 with a common signal rise and with differences in the signal pattern 38', 38" and 38''' is shown in a first diagram 21 as a signal pattern of a measured signal S 35. The measured signal S 35 is scaled on the ordinate. A maximum $A_{Max}$ of the measured signals, a measured signal A selected as an example and exemplarily in the signal rise and measured signals A' selected as examples in the signal pattern 38', A" in the pattern 38" and A''' are shown in a first diagram. The pattern of the control signal 91 is shown over the time course t 400 in the second diagram 22. The control signal 91 is generated by the control unit 3 (FIGS. 1a, 1b, 1c and 1d). The control signal S 35 shows a base signal, which represents the absence of test gas or harmful gas, at the time $t_0$ 410.

A switching signal 91' is sent by the control unit 3 (FIGS. 1a, 1b, 1c and 1d) at a time $t_1$ 401 to the test gas dispensing unit 9 (FIGS. 1a, 1b, 1c and 1d) to dispense or inject a quantity of test substance 5 (FIGS. 1a, 1b, 1c and 1d) to the gas sensor 300, 301, 302, 303 (FIGS. 1a, 1b, 1c and 1d) as a liquid quantity. The quantity of test substance 5 (FIGS. 1a, 1b, 1c and 1d) then evaporates into a quantity of gaseous test gas and is thus available as a test gas for detection by the sensor-measuring arrangement by the gas sensor system 30 (FIGS. 1a, 1b, 1c and 1d). At the time $t_2$ 402, the test gas dispensing unit 9 (FIGS. 1a, 1b, 1c and 1d) is deactivated again by another control signal 91', so that no additional quantity of test substance 5 (FIGS. 1a, 1b, 1c and 1d) is dispensed to the gas sensor system 30 (FIGS. 1a, 1b, 1c and 1d). The measured signal S 35 responds to the dispensing of the quantity of test substance 6 (FIGS. 1a, 1b, 1c and 1d) with a signal rise. The signal rise corresponds to the current change in the gas concentration, caused by the dispensed quantity of gaseous test substance 6 (FIGS. 1a, 1b, 1c and 1d). The signal rise 38 following later reaches a maximum $A_{Max}$ of the measured signals S 35.

In the meantime, the dispensing of the quantity of test substance 5 (FIGS. 1a, 1b, 1c and 1d) was ended by means of the control signal 91". In case of unhindered inflow and outflow (normal case) through the gas admission element 8 (FIGS. 1a, 1b, 1c and 1d), the measured signal S 35 drops over time after the maximum $A_{Max}$. In case the gas admission element 8 (FIGS. 1a, 1d) shows a blockage or an occlusion in the gas supply 7 (FIGS. 1a, 1d) in case of an optical gas sensor 300 (FIG. 1a) or of a semiconductor sensor 303 (FIG. 1d), a signal pattern 38''' is obtained.

In case the gas admission element 8 (FIGS. 1b, 1c) has a blockage in case of a catalytic gas sensor 301 (FIG. 1b) or of an electrochemical gas sensor 302 (FIG. 1c), a signal pattern 38''' is obtained.

The second diagram 22 shows the pattern of the control signal 91 over the time course t 400. This time course t 400 of the second diagram 22 is shown synchronously with the time course t 400 of the first diagram 21. Beginning with a time $t_0$ 410, a control signal 91', which brings about the dispensing of the quantity of test substance 5 (FIGS. 1a, 1b, 1c and 1d), is activated at a time $t_1$ 401. The deactivation of the dispensing of the quantity of test substance 5 (FIGS. 1a, 1b, 1c and 1d) by means of the control signal 91" takes place at the time $t_2$ 402.

In the first diagram 21, the measured signal pattern 38''' shows a pattern that belongs to a sensor-measuring arrangement with an optical gas sensor 300, a decaying measured signal S 35, because an optical gas sensor 300 has no measured gas consumption. As a result, the measured signal S 35 remains nearly constant after dispensing if no gas can escape from the gas sensor 30 (FIGS. 1a, 1b, 1c and 1d) into the measuring environment 2 (FIGS. 1a, 1b, 1c and 1d). The pattern according to 38''' thus shows a drop at which the gas admission element 8 (FIGS. 1a, 1b, 1c and 1d) is closed towards the measuring environment 2 (FIGS. 1a, 1b, 1c and 1d) or is hindered in carrying out gas exchange.

In the first diagram 21, the measured signal pattern 38'' shows a pattern that belongs to a sensor-measuring arrangement with a catalytic gas sensor 301 or to an electrochemical gas sensor 302, a decaying measured signal S 35, which both a catalytic gas sensor 301 and an electrochemical gas sensor 302 have a measured gas consumption. As a result, the measured signal S 35 decays after dispensing even if no gas can escape from the gas sensor 30 (FIGS. 1a, 1b, 1c and 1d) into the measuring environment 2 (FIGS. 1a, 1b, 1c and 1d). The pattern according to 38'' thus shows, just as the pattern according to 38''', a case in which the gas admission element 8 (FIGS. 1a, 1b, ac and 1d) is closed towards the measuring environment 2 (FIGS. 1a, 1b, ac and 1d) or is hindered in carrying out gas exchange. By comparing a signal level of at least one measured signal A', A'', A''' located in time after the maximum $A_{Max}$ in the signal pattern 38, 38', 38'' with the maximum $A_{Max}$, the control unit 3 (FIGS. 1a, 1b, 1c and 1d) determines whether the gas admission element 8 (FIGS. 1a, 1b, 1c and 1d) is closed towards the measuring environment 2 (FIGS. 1a, 1b, 1c and 1d) or is hindered in carrying out gas exchange. The comparison may be carried out, for example and preferably, by forming a weighted or unweighted ratio (quotient, percentage ratio) of the at least one measured signal A', A'', A'' located in time after the maximum $A_{Max}$ in the measured signal pattern 38, 38', 38'' to the maximum or by forming a difference between the at least one measured signal A', A'', A''' with the maximum $A_{Max}$ by means of the control unit 3 (FIGS. 1a, 1b, 1c, ad). In the view according to this FIG. 2, the measured signal A' corresponds to a state of the gas admission element 8 (FIGS. 1a, 1b, 1c and 1d) with an unhindered outflow and inflow from and to the measuring environment 2 (FIGS. 1a, 1b, 1c and 1d). In the view according to this FIG. 2, the measured signal A'' corresponds to a state of the gas admission element 8 (FIGS. 1a, 1b, 1c and 1d) with prevented outflow and/or inflow from/to the measuring environment 2 (FIGS. 1a, 1b, 1c and 1d) in case of a catalytic gas sensor 301 (FIG. 1b) or of an electrochemical gas sensor 302 (FIG. 1c). In the view according to this FIG. 2, the measured signal A''' corresponds to a state of the gas admission element 8 (FIGS. 1a, 1b, 1c and 1d) with prevented outflow and/or inflow from/to the measuring environment 2 (FIGS. 1a, 1b, 1c and 1d) in case of an optical gas sensor 300 (FIG. 1).

While specific embodiments of the invention have been shown and described in detail to illustrate the application of the principles of the invention, it will be understood that the invention may be embodied otherwise without departing from such principles.

APPENDIX

List of Reference Designations 1, 1', 1'', 1''' Gas-measuring arrangement, gas-measuring device
2 Measuring environment
3 Control unit, electronic unit
5 Quantity of test substance (liquid), injected
6 Quantity of test substance (gaseous), evaporated
7 Gas supply
8 Gas admission element, diaphragm, protective grid, flame protection
9 Test gas dispensing unit
21 First diagram
22 Second diagram
30 Gas sensor system
32 Memory (RAM, ROM)
33 Control line
35 Measured signal S, measured signal line
36 Signal transmission unit
38 Measured signal pattern
37 Signal supply unit
40 Acoustic alarm generator (horn)
44 Timer/stop watch/chronometer
50 Optical alarm generator (lamp)
60 Operating and display unit (user interface)
61 Screen element
70 Analysis system
71 Data bank
80 Output unit
81 Interface
91, 91', 91'' Control signal, control signal pattern, control line
92 Signal and data line
300 Optical gas sensor, IR multireflection cell
301 Catalytic gas sensor, heat tone sensor
302 Electrochemical gas sensor
303 Semiconductor gas sensor
304 Valve
305 Test substance reserve, tank, container, cylinder
306 Reserve quantity
400 x axis, time course t
401 Time $t_1$, activation time
402 Time $t_2$, deactivation time
410 Time $t_0$

What is claimed is:
1. A gas-measuring device comprising:
at least one gas sensor with at least one sensor-measuring arrangement, the at least one gas sensor comprising a chamber and a gas sensor housing portion, wherein the at least one gas sensor or a gas-measuring arrangement detects a gas concentration or a change in a gas concentration and the at least one gas sensor or the gas-measuring arrangement comprises a gas admission element arranged upstream of the at least one sensor-measuring arrangement, the at least one sensor-measuring arrangement being located in the chamber, the gas admission element defining a gas permeable interface between an outside measuring environment and the chamber, the gas permeable interface defining a portion of a fluid flow path for a flow of fluid passing from the outside measuring environment into the chamber;
a test gas dispensing unit arranged downstream of the gas admission element in the at least one gas sensor or in the gas-measuring arrangement, the test gas dispensing unit comprising a test gas dispensing unit housing portion arranged outside of the fluid flow path, the test gas dispensing unit housing portion being located at a position located outside of an outer periphery of the gas sensor housing portion; and a control unit and memory associated with the control unit wherein the control unit is programmed to:
  bring about a dispensing of a quantity of test substance directly into an interior of the chamber, by means of the test gas dispensing unit;
  prompt a continuous detection of a plurality of measured signals of the at least one gas sensor and prompt a storage of the plurality of measured signals, as a set of measured signals over a predefined detection time, in the memory and store corresponding time information in the memory for at least some measured signals of the set of measured signals;
  determine a maximum of the measured signals and determine a detection time of the maximum of the measured signals from the set of measured signals;
  select at least one additional measured signal of the at least one gas sensor, which is spaced in time and follows the detection time of the maximum of the measured signals from the set of measured signals, over a predefined detection time on the basis of the time information;
  compare the at least one additional measured signal with the maximum of the measured signals; and
  determine, on the basis of the comparison of the maximum of the measured signals with the at least one additional measured signal, whether the gas admission element is operational to feed air, gas or gas mixture from the outside measuring environment and determining an indicator of operational state of the at least one gas sensor or of the gas-measuring arrangement with the at least one gas sensor or of both the at least one gas sensor and of the gas-measuring arrangement with the at least one gas sensor to operate.

2. The gas-measuring device in accordance with claim 1, wherein the test gas dispensing unit comprises a piezo dispensing element and a reservoir fluidically connected to the piezo dispensing element for storing a reserve quantity, wherein the control unit is configured to activate the piezo dispensing element at a first time, the test gas dispensing unit housing portion comprising an outer peripheral test gas dispensing unit housing portion surface, wherein the outer peripheral test gas dispensing unit housing portion surface is located outside of the flow of fluid.

3. The gas-measuring device in accordance with claim 1, wherein the test gas dispensing unit comprises a valve and a reservoir fluidically connected to the valve for storing a reserve quantity, wherein the control unit is configured to activate the valve at a first time and to deactivate the valve at a second time, the gas sensor housing portion comprising the chamber, the test gas dispensing unit housing portion being located at a position located outside of the chamber, wherein the gas sensor housing portion comprises an opening, the chamber being in fluid communication with the test gas dispensing unit via the opening, the opening being located downstream of the gas permeable interface with respect to the fluid flow path.

4. The gas-measuring device in accordance with claim 3, wherein an output unit has an interface configured and provided to transmit a status signal to an analysis system in interaction with the control unit.

5. The gas-measuring device in accordance with claim 1, further comprising:
  an output unit; and
  an optical alarm generator or an acoustic alarm generator or both an optical alarm generator and an acoustic alarm generator, wherein the optical alarm generator or the acoustic alarm generator are configured and provided to output an alarm signal in interaction with the control unit or with the output unit or both the control unit and the output unit.

6. The gas-measuring device in accordance with claim 1, wherein the at least one sensor-measuring arrangement is configured:
  as a combination of electrodes and an electrolyte in an electrochemical gas sensor;
  as a combination of radiation source and a detector element in an infrared optical gas sensor;
  as a combination of catalytically active or catalytically passive measuring elements or both catalytically active and catalytically passive measuring elements in a catalytic gas sensor or in a heat tone sensor; or
  as a gas species-specific and sensitive semiconductor element in a semiconductor gas sensor.

7. The gas-measuring device in accordance with claim 1, wherein the gas sensor housing portion comprises the chamber, the test gas dispensing unit housing portion being located at a spaced location from the gas sensor housing portion.

8. A gas-measuring device comprising:
  at least one gas sensor with at least one sensor-measuring arrangement, wherein the at least one gas sensor or a gas-measuring arrangement detects a gas concentration or a change in a gas concentration and the at least one gas sensor or the gas-measuring arrangement comprises a gas admission element arranged upstream of the at least one sensor-measuring arrangement, the at least one gas sensor comprising a chamber and a gas sensor housing portion, the gas admission element defining a gas permeable interface between an outside measuring environment and the chamber, the gas permeable interface defining a portion of a fluid flow path for a flow of fluid passing from the outside measuring environment into the chamber;
  a test gas dispensing unit arranged downstream of the gas admission element in the at least one gas sensor or in the gas-measuring arrangement, the test gas dispensing unit comprising a test gas dispensing unit housing portion, wherein the test gas dispensing unit housing portion is located at a position located outside of an outer periphery of the gas sensor housing portion; and
  a control unit and memory associated with the control unit wherein the control unit is programmed to:
  bring about a dispensing of a quantity of test substance directly into an interior of the chamber, by means of the test gas dispensing unit;
  prompt a continuous detection of a plurality of measured signals of the at least one gas sensor and prompt a storage of the plurality of measured signals, as a set of measured signals over a predefined detection time, in the memory and store corresponding time information in the memory for at least some measured signals of the set of measured signals;
  determine a maximum of the measured signals and determine a detection time of the maximum of the measured signals from the set of measured signals;
  select at least one additional measured signal of the at least one gas sensor, which is spaced in time and follows the detection time of the maximum of the measured signals from the set of measured signals, over a predefined detection time on the basis of the time information;
  compare the at least one additional measured signal with the maximum of the measured signals; and determine, on the basis of the comparison of the maximum of the measured signals with the at least one additional measured signal, whether the gas admission element is in a functioning state or a malfunctioning state and determining an indicator of a functioning status of the at least one gas sensor or of the gas-measuring arrangement with the at least one gas sensor or of both the at least one gas sensor and of the gas-measuring arrangement with the at least one gas sensor to operate, the gas admission element feeding air, gas or gas mixture from the outside measuring environment when the gas admission element is in the functioning state.

9. The gas-measuring device in accordance with claim 8, wherein the test gas dispensing unit comprises a piezo dispensing element and a reservoir fluidically connected to the piezo dispensing element for storing a reserve quantity, wherein the control unit is configured to activate the piezo dispensing element at a first time, wherein a lateral test substance flow path is defined by at least the test gas dispensing unit.

10. The gas-measuring device in accordance with claim 8, wherein the test gas dispensing unit comprises a valve and a reservoir fluidically connected to the valve for storing a reserve quantity, wherein the control unit is configured to activate the valve at a first time and to deactivate the valve at a second time, the gas sensor housing portion comprising the chamber, the test gas dispensing unit housing portion being located at a position located outside of the chamber, wherein the gas sensor housing portion comprises an opening, the chamber being in fluid communication with the test gas dispensing unit via the opening, the opening being located downstream of the gas permeable interface with respect to the fluid flow path, the at least one sensor-measuring arrangement being arranged in the chamber.

11. The gas-measuring device in accordance with claim 10, wherein an output unit has an interface configured and provided to transmit a status signal to an analysis system in interaction with the control unit.

12. The gas-measuring device in accordance with claim 8, further comprising:
an output unit; and
an optical alarm generator or an acoustic alarm generator or both an optical alarm generator and an acoustic alarm generator, wherein the optical alarm generator or the acoustic alarm generator are configured and provided to output an alarm signal in interaction with the control unit or with the output unit or both the control unit and the output unit.

13. The gas-measuring device in accordance with claim 8, wherein the at least one sensor-measuring arrangement is configured:
as a combination of electrodes and an electrolyte in an electrochemical gas sensor;
as a combination of radiation source and a detector element in an infrared optical gas sensor;
as a combination of catalytically active or catalytically passive measuring elements or both catalytically active and catalytically passive measuring elements in a catalytic gas sensor or in a heat tone sensor; or
as a gas species-specific and sensitive semiconductor element in a semiconductor gas sensor.

14. A gas-measuring device comprising:
at least one gas sensor with at least one sensor-measuring arrangement, wherein the at least one gas sensor or a gas-measuring arrangement detects a gas concentration or a change in a gas concentration and the at least one gas sensor or the gas-measuring arrangement comprises a gas admission element arranged upstream of the at least one sensor-measuring arrangement, the at least one gas sensor comprising a chamber and a gas sensor housing portion, the gas admission element defining a permeable interface between an outside measuring environment and the chamber, wherein a fluid flow path is defined by at least the permeable interface for a flow of fluid passing from the outside measuring environment to the chamber;
a test gas dispensing unit arranged downstream of the gas admission element in the at least one gas sensor or in the gas-measuring arrangement, the test gas dispensing unit comprising a test gas dispensing unit housing portion located at a position outside of an outer periphery of the gas sensor housing portion; and
a control unit and memory associated with the control unit wherein the control unit is programmed to:
bring about a dispensing of a quantity of test substance directly into an interior of the chamber, by means of the test gas dispensing unit, wherein the quantity of test substance is dispensed between the gas admission element and the at least one sensor-measuring arrangement via the test gas dispensing unit;
prompt a continuous detection of a plurality of measured signals of the at least one gas sensor and prompt a storage of the plurality of measured signals, as a set of measured signals over a predefined detection time, in the memory and store corresponding time information in the memory for at least some measured signals of the set of measured signals;
determine a maximum of the measured signals and determine a detection time of the maximum of the measured signals from the set of measured signals;
select at least one additional measured signal of the at least one gas sensor, which is spaced in time and follows the detection time of the maximum of the measured signals from the set of measured signals, over a predefined detection time on the basis of the time information;
compare the at least one additional measured signal with the maximum of the measured signals; and
determine an operating state of the gas admission element based on whether the dispensed quantity of the test substance has exited the at least one gas sensor after a predetermined time based on the comparison of the maximum of the measured signals with the at least one additional measured signal.

15. The gas-measuring device in accordance with claim 14, wherein the test gas dispensing unit comprises a piezo dispensing element and a reservoir fluidically connected to the piezo dispensing element for storing a reserve quantity, wherein the control unit is configured to activate the piezo dispensing element at a first time.

16. The gas-measuring device in accordance with claim 14, wherein the test gas dispensing unit comprises a valve and a reservoir fluidically connected to the valve for storing a reserve quantity, wherein the control unit is configured to activate the valve at a first time and to deactivate the valve at a second time, the gas sensor housing portion comprising the chamber, the test gas dispensing unit housing portion being located at a position located outside of the chamber, wherein the gas sensor housing portion comprises an opening, the chamber being in fluid communication with the test gas dispensing unit via the opening, the opening being located downstream of the permeable interface with respect to the fluid flow path, the at least one sensor-measuring arrangement being arranged in the chamber.

17. The gas-measuring device in accordance with claim 16, wherein an output unit has an interface configured and provided to transmit a status signal to an analysis system in interaction with the control unit.

18. The gas-measuring device in accordance with claim 14, further comprising:
an output unit; and
an optical alarm generator or an acoustic alarm generator or both an optical alarm generator and an acoustic alarm generator, wherein the optical alarm generator or the acoustic alarm generator are configured and provided to output an alarm signal in interaction with the control unit or with the output unit or both the control unit and the output unit.

19. The gas-measuring device in accordance with claim 14, wherein the at least one sensor-measuring arrangement is configured:

as a combination of electrodes and an electrolyte in an electrochemical gas sensor;

as a combination of radiation source and a detector element in an infrared optical gas sensor;

as a combination of catalytically active or catalytically passive measuring elements or both catalytically active and catalytically passive measuring elements in a catalytic gas sensor or in a heat tone sensor; or as a gas species-specific and sensitive semiconductor element in a semiconductor gas sensor.

20. The gas-measuring device in accordance with claim 14, wherein the gas sensor housing portion comprises the chamber, the test gas dispensing unit housing portion being located at a spaced location from the gas sensor housing portion.

* * * * *